US006258942B1

(12) United States Patent
O'Brien et al.

(10) Patent No.: US 6,258,942 B1
(45) Date of Patent: Jul. 10, 2001

(54) TADG7: A NOVEL GENE EXPRESSED IN OVARIAN TUMOR AND USES THEREOF

(75) Inventors: Timothy J. O'Brien, Little Rock, AR (US); Sung Moon, Seoul (KR)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 08/926,808

(22) Filed: Sep. 9, 1997

(51) Int. Cl.[7] ..................................................... C07H 21/04
(52) U.S. Cl. ........................ 536/23.1; 536/23.5; 435/91.1
(58) Field of Search ........................... 435/91.1; 536/23.5

(56) References Cited

PUBLICATIONS

Hillier et al Genome Research vol. 6 807–828, 1996.*
Ausubel et al Current Protocols in Molecular Biology Chapter 16 pp. 16.0.1 through 16.2.1, 1990.*

* cited by examiner

*Primary Examiner*—Julie Burke

(74) *Attorney, Agent, or Firm*—Benjamin Aaron Adler

(57) ABSTRACT

The invention is a protein having the amino acid sequence of Seq. I.D. No. 1 or an allelic variation retaining the biological activity of the protein having the amino acid sequence of Seq. I.D. No. 1, a DNA segment coding for a protein according to claim 1, preferably DNA segment according to claim 2 having the sequence of Seq. I.D. No. 2, or a substitution analog or allelic variation of Seq. I.D. No. 2, a chimeric cell comprising the DNA segment coding for a protein of Seq. I.D. No. 1, preferably a chimeric cell comprising the DNA segment of Seq. I.D. No. 2, a vector comprising a DNA segment coding for a protein having Seq. I.D. No. 1 operably linked to a promoter. The invention provides a preferred vector comprising the following components operably linked from 5' to 3': (a) a promoter; (b) a signal sequence; (c) 5' portion of a highly expressed gene endogenous to a selected host cell; (d) a linker sequence; all preceding the nucleotide sequence coding for TADG7 protein. The invention provides a protein production method which comprises expressing a DNA segment coding for a protein with the amino acid sequence of Seq. I.D. No. 1 in a chimeric host cell, preferably one which comprises expressing the DNA segment having the sequence of Seq. I.D. No. 2 or a substitution analog. The protein may play a role in signal transduction. The invention provides a means for early detection of ovarian cancer.

8 Claims, 16 Drawing Sheets

```
  1 GATGCGTACC CGGGGCAGAT TGGCAGGACA AGTGGGAGCA GATGGCCTGC
    Primer p34B -‡

51 CTTTGGCTGA GAGGGCTACC TGCCCAGCCC CTCCCCCAAC AAGATCTCTT

101 GGACTCAGGC CTCAGAGCCT GGCCTGGTTN TNAGTGTGTG TCCCTGTGTG

151 TGTGTTGCNN NNNNNNNNNN NNNNNNNNNN NNNNNNNNNN NNNNNNNNNN (201 NN. . . . . . . . . . . . . . . NN 450)

451 NNNNNNNNNN NNNNNNNNNN NNNNNNNNNN NNCAGTCTCT TCCCCAAAGT

501 CTCACCTTTT CTTCAATAGA AAATTCCGCT TGACCTTTGG TGACTGCCCA

551 CTTNCCAGCT CCACTGGCCC AAGTCTGAGC CGGAGGCCCT TGTTTTGGGG

601 GCGGGGGGAG AGTTGGATGT GATTGCCCTT GAAGAACAAG GCTGACCTGA

651 GAGGTNCCTG GCGCCCTGAG GTGGCTCAGC ATCTGCCCGG GATACGCGTC
              (3'<--- 5': TAGACGGGCC CTATGCGCAG)
                                  <--- Primer p34B
                                                |
                                              `700
```

Fig. 2

```
   1  AGTCATCGTCCCTTTATCGGCACCCCCTTGTTGGAGATGGAGGCAGCAGA
  51  CGTGCAGTGCCATAAGGTGCCCCAGTCCTTCTGGAGGCCTGGGCTGCTAC
 101  TGTTGGCCACCCTGTGTCTAGTGATGCTCTCTGTGCTCACCTCCTAGGCC
 151  ATGGAGCCTGAGGGGCCTGCACCGGGTTTGCTGAAACTGACAGAGCCTG
 201  GGCTCCAGACCTCTCTCCCTCCTACAGTGCTCTCCCTCCCTGGGCAGATT
 251  GGCAGGACAAGTGGGAGCAGATGGCCTGCCTTTGGCTGAGAGGGCTACCT
 301  GCCCAGCCCCTCCCCCAACAAGATCTCTTGGACTCAGGCCTCAGAGCCTG
 351  GCCTGGTTGTGAGTGTGTGTCCCTGTGTGTGTTGCGGGAGGGGAGGAC
 401  TGGGGCTGGAAGTCCAGCACCCAGGGAAGATCTGTCCTCCTGTTCTTGGG
 451  AAGCGTTTGCCTGACGGCTTCTCGGCTCTACCCTCACCCTTCTGGCCAGG
 501  ATCCCGCAGGGCAACAGCCCCATCTGCTTGGCTGACCCCACACCCAGGAC
 551  CACTGTCCGGCTCTAACACAGCTATTAAGTGCTACCTGCCTCTCAGGCAC
 601  TCTCCTCGCCCAGTTTCTGAGGTCAGACGAGTGTCTGCGATGTCTTCCCG
 651  CACTCTATTCCCCCAGCCTCTTTCTGCTTTCATGCTCAGCACATCATCTT
 701  CCTAGGCAGTCTCTTCCCCAAAGTCTCACCTTTTCTTCCAATAGAAAATT
 751  CCGCTTGACCTTTGGTGCACTGCCCACTTCCCAGCTCCACTGGCCCAAGT
 801  CTGAGCCGGAGGCCCTTGTTTTGGGGGCGGGGGGAGAGTTGGATGTGATT
 851  GCCCTTGAAGAACAAGGCTGACCTGAGAGGTTCCTGGCGCCCTGAGGTGG
 901  CTCAGCACCTGCCCAGGGTAGGCCTGGCATGAGGGGTTAGGTCAGCCAAT
 951  GTCAGCTGCTTCTCTTGGGGCCCTCAGAGTCTATCTCCCCAAGACAGG
1001  AAGGGAAAAGCAAATTTCTAATTCACCAGCAATAAAAATTGGAGGAGGCT
1051  TGGCCCTCAGCCCTTATATCTCCCTCTTTTTCACTCTCTTCCTCCCACCC
1101  CCAAGACTGAGTTTTGGGGGGCAAGGTGGAGAGAGCTGGCAACTACTGTG
1151  AGCAAGTCCCCTAGCCCCTGACCAGCCTCCTCCCATGACTGGTGACTGTT
1201  TAATGAGCTGTGCATCCCCACAAAACATGAGTGCCCCTCTGTGTGGCC
1251  TCTAACCCTCTGCACAGCCCATCTGGGTGGTCCTCACCAGGTCTCAGAGC
1301  TGGGTGGGAGGCCATCCTGGCGACCACTGCCCATTCCATTCACCCCTCAC
1351  TGTACCTGCCCTAGAACCTGGGCCTAGGCCACAGGGGCAGGGAGAAGAGA
1401  AGGCATTAGTAAGAAAAAATAGAAAAAAATATGAACAGACTCAGCTTTG
1451  GGACGTCCAACCACAAAAGGAATTATATATAAATATATATAAATATATAT
1501  CTCTACCATATGTGATGGAGAGACTTTTTGTTTTCCTTTCCCAAAGAAAT
1551  AAAACGGAAAAGCCTCTTGAGTGGTAAAAAAAAAAAAAAAAAAAAAAAA
1601  AAAAAAAA      1609
```

Fig. 9

```
  1 AGTCATCGTCCCTTTATCGGCACCCCCTTGTTGGAGATGGAGGCAGCAGA
    CGTGCAGTGCCATAAGGTGCCCCAGTCCTTCTGGAGGCCTGGGCTGCTAC
    TGTTGGCCACCCTGTGTCTAGTGATGCTCTCTGTGCTCACCTCCTAGGCC

151 ATGGAGCCTGAGGGGGCCTGCACCGGGTTTGCTGAAACTGACAGAGCCTGG
     M   E   P   E   G   A   C   T   G   F   A   E   T   D   R   A   W
    GCTCCAGACCTCTCTCCCTCCTACAGTGCTCTCCCTCCCTGGGCAGATTGG
     A   P   D   L   S   P   S   Y   S   A   L   P   P   W   A   D   W
    CAGGACAAGTGGGAGCAGATGGCCTGCCTTTGGCTGAGAGGGCTACCTGCC
     Q   D   K   W   E   Q   M   A   C   L   W   L   R   G   L   P   A
    CAGCCCCTCCCCCAACAAGATCTCTTGGACTCAGGCCTCAGAGCCTGGCCT
     Q   P   L   P   Q   Q   D   L   L   D   S   G   L   R   A   W   P
    GGTTGTGAGTGTGTGTCCCTGTGTGTGTGTTGCGGGAGGGGAGGACTGGGG
     G   C   E   C   V   S   L   C   V   C   G   R   G   G   L   G
    CTGGAAGTCCAGCACCCAGGGAAGATCTGTCCTCCTGTTCTTGGGAAGCGT
     L   E   V   Q   H   P   G   K   I   C   P   P   V   L   G   K   R
    TTGCCTGACGGCTTCTCGGCTCTACCCTCACCCTTCTGGCCAGGATCCCGC
     C   L   T   A   F   S   A   L   P   S   P   F   W   P   G   S   R
    AGGGCAACAGCCCCATCTGCTTGGCTGACCCCACACCCAGGACCACTGTCC
     R   A   T   A   P   S   A   W   L   T   P   H   G   P   L   S
    GGCTCTAACACAGCTATTAAGTGCTACCTGCCTCTCAGGCACTCTCCTCGC
     G   S   N   T   A   I   K   C   Y   L   P   L   R   H   S   P   R
    CCAGTTTCTGAGGTCAGACGAGTGTCTGCGATGTCTTCCCGCACTCTATTC
     P   V   S   E   V   R   R   V   S   A   M   S   S   R   T   L   F
    CCCCAGCCTCTTTCTGCTTTCATGCTCAGCACATCATCTTCCTAG 705
     P   Q   P   L   S   A   F   M   L   S   T   S   S   *

706 GCAGTCTCTTCCCCAAAGTCTCACCTTTTCTTCCAATAGAAAATTCCGCT
    TGACCTTTGGTGCACTGCCCACTTCCCAGCTCCACTGGCCCAAGTCTGAG
    CCGGAGGCCCTTGTTTTGGGGGCGGGGGGAGAGTTGGATGTGATTGCCCT
    TGAAGAACAAGGCTGACCTGAGAGGTTCCTGGCGCCCTGAGGTGGCTCAG
    CACCTGCCCAGGGTAGGCCTGGCATGAGGGGTTAGGTCAGCCAATGTCAG
    CTGCTTCTCTTGGGGCCCTCTCAGAGTCTATCTCCCCAAGACAGGAAGGG
    AAAAGCAAATTTCTAATTCACCAGCAATAAAAATTGGAGGAGGCTTGGCC
    CTCAGCCCTTATATCTCCCTCTTTTTCACTCTCTTCCTCCCACCCCCAAG
    ACTGAGTTTTGGGGGGCAAGGTGGAGAGAGCTGGCAACTACTGTGAGCAA
    GTCCCCTAGCCCCTGACCAGCCTCCTCCCATGACTGGTGACTGTTTAATG
    AGCTGTGCATCCCCACAAAACATGAGTGCCCTCTGTGTGGCCTCTAA
    CCCTCTGCACAGCCCATCTGGGTGGTCCTCACCAGGTCTCAGAGCTGGGT
    GGGAGGCCATCCTGGCGACCACTGCCCATTCCATTCACCCCTCACTGTAC
    CTGCCCTAGAACCTGGGCCTAGGCCACAGGGGCAGGGAGAAGAGAAGGCA
    TTAGTAAGAAAAAATAGAAAAAATATGAACAGACTCAGCTTTGGGACG
    TCCAACCACAAAGGAATTATATATAAATATATATAAATATATATCTCTA
    CCATATGTGATGGAGAGACTTTTTGTTTTCCTTTCCCAAAGAAATAAAAC
    GGAAAAGCCTCTTGAGTGGTAAAAAAAAAAAAAAAAAAAAAAAAAAAA
    AAAA 1609
```

Fig. 10

```
                          1*
  1     MEPEGACTGF     AETDRAWAPD     LSPSYSALPP
              ...
              3
 31     WADWQDKWEQ     MACLWLRGLP     AQPLPQQDLL
                       5===============
 61     DSGLRAWPGC     ECVSLCVCCG     RGGLGLEVQH
                                4
                                         1*
 91     PGKICPPVLG     KRLPDGFSAL     PSPFWPGSRR
                                          ...
                                          3
         2•
121     .ATAPSAWLTP    HPGPLSGSNT ... AIKCYLPLRH
         ..                                 3
         1*             2• 1*
151     SPRPVSEVRR     VSAMSSRTLF     PQPLSAFMLS
181     TSSS    184
```

1: Phosphorylation site: Protein Kinase C

2: Phosphorylation site: Protein Kinase (cAMP dependent)

3: Myristylation site: Consensus GxxxGx

4: RTK (Protein Kinase) Signature: ATP-binding Site Consensus G xGxxG (s) 14 ~ 23 K (80 - 101)

5: RTK Signature: Class III
   MxCxxx GxP (41 - 53)
       L
       I
       V

Fig. 12

```
                       SEQUENCE LISTING ( 1 ) GENERAL INFORMATION:

( iii ) NUMBER OF SEQUENCES: 7

( 2 ) INFORMATION FOR SEQ ID NO: 1:

( i ) SEQUENCE CHARACTERISTICS:
            ( A ) LENGTH:        184 AMINO ACIDS
            ( B ) TYPE:          AMINO ACID
            ( C ) STRANDEDNESS:  SINGLE
            ( D ) TOPOLOGY:      LINEAR ( ii ) MOLECULE TYPE:       PROTEIN ( xi ) SEQUENCE DESCRIPTION: SEQ ID NO: 1:

Met Glu Pro Glu Gly Ala Cys Thr Gly Phe
                 5                   10

Ala Glu Thr Asp Arg Ala Trp Ala Pro Asp
                15                   20

Leu Ser Pro Ser Tyr Ser Ala Leu Pro Pro
                25                   30

Trp Ala Asp Trp Gln Asp Lys Trp Glu Gln
                35                   40

Met Ala Cys Leu Trp Leu Arg Gly Leu Pro
                45                   50

Ala Gln Pro Leu Pro Gln Gln Asp Leu Leu
                55                   60

Asp Ser Gly Leu Arg Ala Trp Pro Gly Cys
                65                   70

Glu Cys Val Ser Leu Cys Val Cys Cys Gly
                75                   80

Arg Gly Gly Leu Gly Leu Glu Val Gln His
                85                   90

Pro Gly Lys Ile Cys Pro Pro Val Leu Gly
                95                  100

Lys Arg Leu Pro Asp Gly Phe Ser Ala Leu
               105                  110

Pro Ser Pro Phe Trp Pro Gly Ser Arg Arg
               115                  120
```

```
Ala Thr Ala Pro Ser Ala Trp Leu Thr Pro
            125                 130

His Pro Gly Pro Leu Ser Gly Ser Arg Cys
            135                 140

Ala Ile Lys Cys Tyr Leu Pro Leu Arg His
            145                 150

Ser Pro Arg Pro Val Ser Glu Val Arg Arg
            155                 160

Val Ser Ala Met Ser Ser Arg Thr Leu Phe
            165                 170

Pro Gln Pro Leu Ser Ala Phe Met Leu Ser
            175                 180

Thr Ser Ser Ser
            184
```

(2) INFORMATION FOR SEQ ID NO: 2:

(i) SEQUENCE CHARACTERISTICS:
        (A) LENGTH: 1609 BASE PAIRS
        (B) TYPE: NUCLEIC ACID
        (C) STRANDEDNESS: SINGLE
        (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 2:

```
AGTCATGCTC CCTTTATCGG CACCCCCTTG TTGGAGATGG AGGCAGCAGA         50

CGTGCAGTGC CATAAGGTGC CCCAGTCCTT CTGGAGGCCT GGGCTGCTAC        100

TGTTGGCCAC CCTGTGTCTA GTGATGCTCT CTGTGCTCAC CTCCTAGGCC        150

ATGGAGCCTG AGGGGCCTG CACCGGGTTT GCTGAAACTG ACAGAGCCTG         200

GGCTCCAGAC CTCTCTCCCT CCTACAGTGC TCTCCCTCCC TGGGCAGATT        250

GGCAGGACAA GTGGGAGCAG ATGGCCTGCC TTTGGCTGAG AGGGCTACCT        300

GCCCAGCCCC TCCCCCAACA AGATCTCTTG GACTCAGGCC TCAGAGCCTG        350

GCCTGGTTGT GAGTGTGTGT CCCTGTGTGT GTGTTGCGGG AGGGGAGGAC        400

TGGGGCTGGA AGTCCAGCAC CCAGGGAAGA TCTGTCCTCC TGTTCTTGGG        450

AAGCGTTTGC CTGACGGCTT CTCGGCTCTA CCCTCACCCT TCTGGCCAGG        500

ATCCCGCAGG GCAACAGCCC CATCTGCTTG GCTGACCCCA CACCCAGGAC        550

CACTGTCCGG CTCTAACACA GCTATTAAGT GCTACCTGCC TCTCAGGCAC        600

TCTCCTCGCC CAGTTTCTGA GGTCAGACGA GTGTCTGCGA TGTCTTCCCG        650

CACTCTATTC CCCCAGCCTC TTTCTGCTTT CATGCTCAGC ACATCATCTT        700

CCTAGGCAGT CTCTTCCCCA AAGTCTCACC TTTTCTTCCA ATAGAAAATT        750

CCGCTTGACC TTTGGTGCAC TGCCCACTTC CCAGCTCCAC TGGCCCAAGT        800

CTGAGCCGGA GGCCCTTGTT TTGGGGGCGG GGGAGAGTT GGATGTGATT         850

GCCCTTGAAG AACAAGGCTG ACCTGAGAGG TTCCTGGCGC CCTGAGGTGG        900

CTCAGCACCT GCCCAGGGTA GGCCTGGCAT GAGGGGTTAG GTCAGCCAAT        950

GTCAGCTGCT TCTCTTGGGG CCCTCTCAGA GTCTATCTCC CCAAGACAGG       1000

AAGGGAAAAG CAAATTTCTA ATTCACCAGC AATAAAAATT GGAGGAGGCT       1050
```

```
TGGCCCTCAG CCCTTATATC TCCCTCTTTT TCACTCTCTT CCTCCCACCC        1100

CCAAGACTGA GTTTTGGGGG GCAAGGTGGA GAGAGCTGGC AACTACTGTG        1150

AGCAAGTCCC CTAGCCCCTG ACCAGCCTCC TCCCATGACT GGTGACTGTT        1200

TAATGAGCTG TGCATCCCCC ACAAAAACAT GAGTGCCCCT CTGTGTGGCC        1250

TCTAACCCTC TGCACAGCCC ATCTGGGTGG TCCTCACCAG GTCTCAGAGC        1300

TGGGTGGGAG GCCATCCTGG CGACCACTGC CCATTCCATT CACCCCTCAC        1350

TGTACCTGCC CTAGAACCTG GGCCTAGGCC ACAGGGCAG GGAGAAGAGA         1400

AGGCATTAGT AAGAAAAAAA TAGAAAAAAA TATGAACAGA CTCAGCTTTG        1450

GGACGTCCAA CCACAAAAGG AATTATATAT AAATATATAT AAATATATAT       1500

CTCTACCATA TGTGATGGAG AGACTTTTTG TTTTCCTTTC CCAAAGAAAT        1550

AAAACGGAAA AAGCCTCTTG AGTGGTAAAA AAAAAAAAAA AAAAAAAAA        1600

AAAAAAAAA                                                      1609

(2) INFORMATION FOR SEQ ID NO: 3:

(i) SEQUENCE CHARACTERISTICS:
        (A) LENGTH: 158 BASES
        (B) TYPE: NUCLEIC ACID
        (C) STRANDEDNESS: SINGLE
        (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 3:

GATGCGTACC CGGGGCAGAT TGGCAGGACA AGTGGGAGCA GATGGCCTGC          50

CTTTGGCTGA GAGGGCTACC TGCCCAGCCC CTCCCCCAAC AAGATCTCTT         100

GGACTCAGGC CTCAGAGCCT GGCCTGGTTN TNAGTGTGTG TCCCTGTGTG         150

TGTGTTGC                                                       158

(2) INFORMATION FOR SEQ ID NO: 4:

(i) SEQUENCE CHARACTERISTICS:
        (A) LENGTH: 238 BASE PAIRS
        (B) TYPE: NUCLEIC ACID
        (C) STRANDEDNESS: SINGLE
        (D) TOPOLOGY: LINEAR (ii) MOLECULE TYPE: OTHER NUCLEIC ACID (iii) HYPOTHETICAL: NO (iv) ANTI-SENSE: YES (xi) SEQUENCE DESCRIPTION: SEQ ID NO: 4:

CAGTCTCTTC CCCAAAGTCT CACCTTTTCT TCAATAGAAA ATTCCGCTTG          50

ACCTTTGGTG ACTGCCCACT TNCCAGCTCC ACTGGCCCAA GTCTGAGCCG         100

GAGGCCCTTG TTTTGGGGGC GGGGGAGAG TTGGATGTGA TTGCCCTTGA          150

AGAACAAGGC TGACCTGAGA GGTNCCTGGC GCCCTGAGGT GGCTCAGCAT         200

CTGCCCGGGA TACGCGTCTA GACGGGCCCT ATGCGCAG                      238
```

```
(2) INFORMATION FOR SEQ ID NO: 5:

(i) SEQUENCE CHARACTERISTICS:
        (A) LENGTH: 12 AMINO ACIDS
        (B) TYPE: AMINO ACID
        (C) STRANDEDNESS:  SINGLE
        (D) TOPOLOGY:  LINEAR (ii) MOLECULE TYPE: peptide (iii) HYPOTHETICAL: NO (iv) ANTI-SENSE:

(xi) SEQUENCE DESCRIPTION: SEQ ID NO: 5:

Thr Pro Phe Pro Gly Pro Leu Ser Gly Ser
                 5                   10

Asn Thr
    12

(2) INFORMATION FOR SEQ ID NO: 6:

(i) SEQUENCE CHARACTERISTICS:
        (A) LENGTH: 20 BASES
        (B) TYPE:  NUCLEIC ACID
        (C) STRANDEDNESS:  SINGLE
        (D) TOPOLOGY:  LINEAR (ii) MOLECULE TYPE:  OTHER NUCLEIC ACID (iii) HYPOTHETICAL:  NO (iv) ANTI-SENSE:  NO (xi) SEQUENCE DESCRIPTION: SEQ ID NO: 6:

GATGCGTACC CGGGGCAGAT                                                          20

(2) INFORMATION FOR SEQ ID NO: 7:

(i) SEQUENCE CHARACTERISTICS:
        (A) LENGTH: 20 BASES
        (B) TYPE:  NUCLEIC ACID
        (C) STRANDEDNESS:  SINGLE
        (D) TOPOLOGY:  LINEAR (ii) MOLECULE TYPE:  OTHER NUCLEIC ACID (iii) HYPOTHETICAL:  NO (iv) ANTI-SENSE:  NO (xi) SEQUENCE DESCRIPTION: SEQ ID NO: 7:

TAGACGGGCC CTATGCGCAG                                                          20
```

TADG7: A NOVEL GENE EXPRESSED IN OVARIAN TUMOR AND USES THEREOF

TECHNICAL FIELD

The present invention encompasses a novel protein designated tumor associated diagnostic gene 7 (TADG7), a novel TADG7 cDNA and mRNA segments coding for the TADG7 protein, chimeric cells comprising the TADG7 DNA segment, vectors and plasmids comprising the TADG7 DNA segment and methods for producing the TADG7 protein as well as methods for detection and use of measurement of the expression of the gene coding for the TADG7 protein as a diagnostic tool in early detection of ovarian cancer. Measurement methods may detect either the TADG7 mRNA, or the TADG7 protein. Novel antibodies useful in detection and purification of the TADG7 protein are also provided.

BACKGROUND OF THE INVENTION

Proteins involved in cell cycle regulation containing various characteristic regions have been previously identified. For example, protein tyrosine kinases comprising SH3 and SH2 domains are disclosed in U.S. Pat. No. 5, 439,819. Proteins including SH2 and SH3 domains have been found to be important in cell cycle processes, especially in signal transduction pathways. Receptor tyrosine kinases are known participants in signal transduction processes. Numerous proteins involved in signal transduction are discussed by Fantl et al., Ann. Rev. Biochem. (1993), 62:453, Dohlwan, et al., Ann. Rev. Biochem. (1991), 60:653; and Simon et al., Cell (1993), 73:169. Over expression of cell cycle proteins has been observed in numerous tumors, and often serves as a diagnostic tool.

Interfering in the intracellular signal transduction pathways may provide a mechanism for numerous therapeutic applications. While several proteins have been identified that interfere with various signal transduction mechanisms, new active proteins are important in providing alternatives for therapy and drug development. The novel protein of the invention provides a heretofore unknown molecule that is useful as a diagnostic marker in ovarian tumors. The gene is also expressed in brain tissue and may play a role in signal processing in the brain.

Two partial DNA sequences entered into a database of so-called expressed sequence tags (EST) have 97% and 96% homology over approximately 405 and 374 nucleotides to the 3' end of the TADG7 gene. These fragmentary sequences do not in themselves provide any clues as to either the nature or use of the TADG7 protein, or its sequence, or the DNA sequence of the complete gene.

SUMMARY OF THE INVENTION

The invention is a novel TADG7 protein having the amino acid sequence set out in Seq. I.D. No. 1, novel TADG7 cDNA and mRNA segments coding for the TADG7 protein, isolated from human genetic material. The cDNA sequence is set out in Seq. I.D. No. 2, the mRNA is set out in Seq. I.D. No. 3. The invention in another embodiment includes a construct comprising the open reading frame found at base 151 (beginning the initial methionine codon) to base 1548 or optionally through base 1553 (end of the polyadenylation sequence downstream of the open reading frame), or a sequence analog there of. Preferably the open reading frame segment 151 to 1548 or 1553 is coupled with a promoter segment and optionally coupled with additional DNA coding for a fusion protein segment useful in purification such as a poly histidine tail or an enzyme such as GST. Such an embodiment of the subject invention may comprise one or more of the following components operably linked from 5' to 3' to form an expression plasmid vector: (a) a promoter; (b) a signal sequence, (c) 5' portion of a highly expressed endogenous gene preferably one whose product is secreted from the host cells (i.e. glucoamylase gene in Aspergillis); (d) a linker sequence; and (e) a nucleotide sequence corresponding to the desired TADG7 protein or a TADG7 polypeptide fragment. Alternatively a resistance selectable marker gene may also be inserted after the TADG7 nucleotide sequence, following a transcription termination sequence, and having the appropriate components to function as a means for selecting clones containing the vector. In an alternative embodiment expression level of the cDNA, measured either by quanitation of TADG7 mRNA or detection of the TADG7 protein in a tumor specimen to be characterized provide a diagnostic method for detection of ovarian carcinomas.

In additional embodiments the invention also provides chimeric cells adapted to express the TADG7 protein, which preferably comprise vectors constructed as described above. The vectors may also include DNA coding for TADG7 fusion proteins. The invention further provides methods for production of the TADG7 protein including expression of the TADG7 DNA or substitution analogs thereof in chimeric cells.

The TADG7 protein comprises regions with overall homology with members of the receptor tyrosine kinase (RTK) subfamily, particularly RTK Class III of the protein kinase family. These regions augment the utility of the protein, DNA and mRNA as diagnostic tools. Of course the protein is useful as a source of amino acids, as a nutrition supplement, and as a marker for human tissue, as well as having potential therapeutic uses due to its primary role in cell cycle control. In addition, the protein itself or specific peptides generated from the protein sequence could be used as antigens for the production of polyclonal and monoclonal antibodies useful in tissue typing and tumor diagnostics. Further, the gene itself can be used as an antisense vehicle for cell cycle control by shutting down signaling or cell division.

BRIEF DESCRIPTION OF THE DRAWINGS

The features and advantages of this invention will be evident from the following description when read in conjunction with the accompanying drawings:

FIG. 2 illustrates the sense nucleotide sequence of the TADG7 gene fragment amplified and sequenced, the PCR primers being identified by underscore at both the 5' and 3' ends.

FIG. 9 is the sequence of Seq. I.D. No. 2, the sense stands sequence of the 1609 base pair TADG7 gene.

FIGS. 10A and 10B show the sequence of TADG7 gene, which contains the open reading frame (ORF) coding for 184 amino acids spanning nucleotides 151 through 705.

FIG. 12 illustrates the TADG7 protein sequence of Seq. I.D. No. 1, including an RTK protein kinase signature ATP binding site consensus sequence, a potential RTK signature sequence for class III RTKs, three potential myristalation sites, four potential phosphorylation sites for protein kinase C and two potential phosphorylation sites for cyclic-AMP-dependent protein kinase.

DETAILED DESCRIPTION OF THE INVENTION

The subject invention encompasses a novel protein TADG7 represented by its amino acid sequence (Seq. I.D. No. 1), a sense TADG7 DNA segment (Seq. I.D. No. 2) coding for the TADG7 protein, replacement analogs of the sense TADG7 DNA also coding for the TADG7 protein but having replacement of codons with other codons coding for the same amino acids, the corresponding mRNA sequence characteristic of expression of the TADG7 gene or substitution analogs thereof, vectors and plasmids comprising a DNA segment coding for the TADG7 protein. Another embodiment of the subject invention comprises the following components operably linked from 5' to 3' to form an expression plasmid vector: (a) a promoter; (b) a signal sequence, (c) 5' portion of a highly expressed endogenous gene preferably one whose product is secreted from the host cells (i.e. glucoamylase gene in Aspergillis); (d) a linker sequence; and (e) a nucleotide sequence corresponding to the desired TADG7 protein or TADG7. Preferably the vector also includes a selectable marker gene such as a resistance gene. The invention also provides chimeric cells comprising a DNA segment coding for the TADG7 protein, and a method for producing the TADG7 protein as well as a method for using the TADG7 protein. In a final embodiment early and late stage ovarian carcinomas are identified by high levels of expression of TADG7 relative to a reference protein such as β tubulin and may be screened by the detection of the TADG7 mRNA, cDNA or protein in the tissues. The examples and description below further define the various embodiments of the invention.

Gene Isolation

Figure 1:
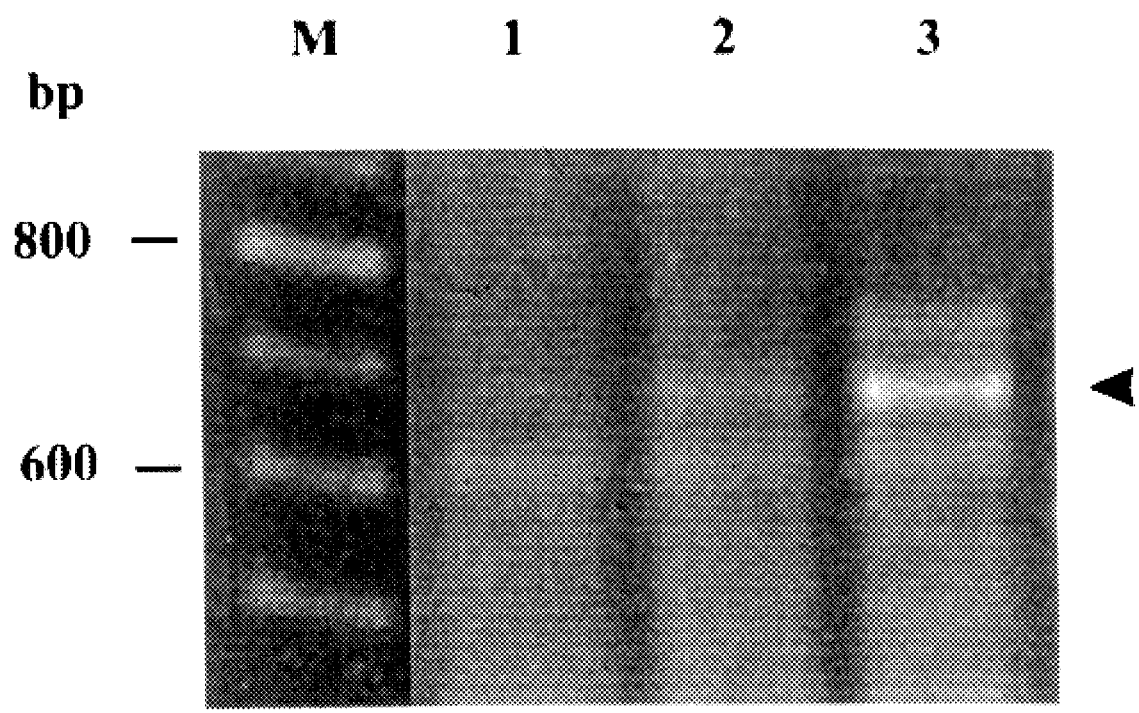
FIG. 1 is a PCR result showing that the TADG7 gene is differentially expressed in normal ovary, low malignant potential tumor, and ovarian carcinoma tissues by measurement to the corresponding mRNA.
Figure 3A:
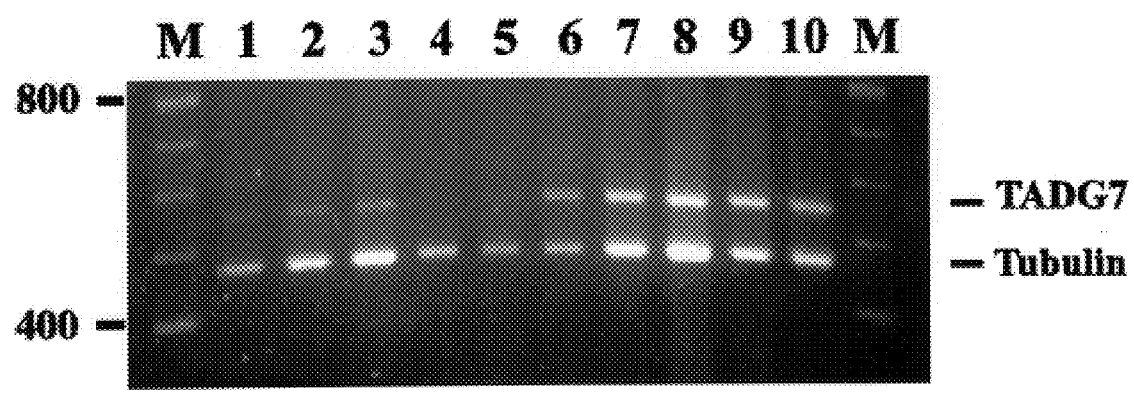
FIG. 3a compares expression levels of TADG7 with β-tubulin in 5 normal ovary samples (Lanes 1–5) and 5 ovarian carcinoma samples (Lanes 6–10).
Figure 3B:
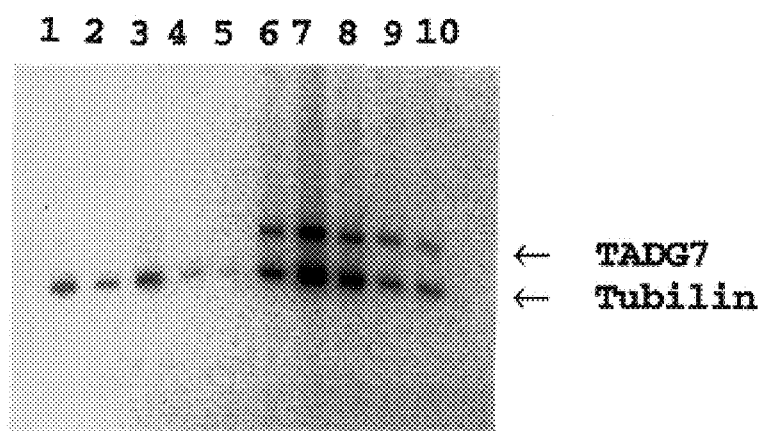
FIG. 3b shows the $p^{32}$ incorporation data for phospho-imager analysis of normal versus carcinoma tissue.
Figure 4:
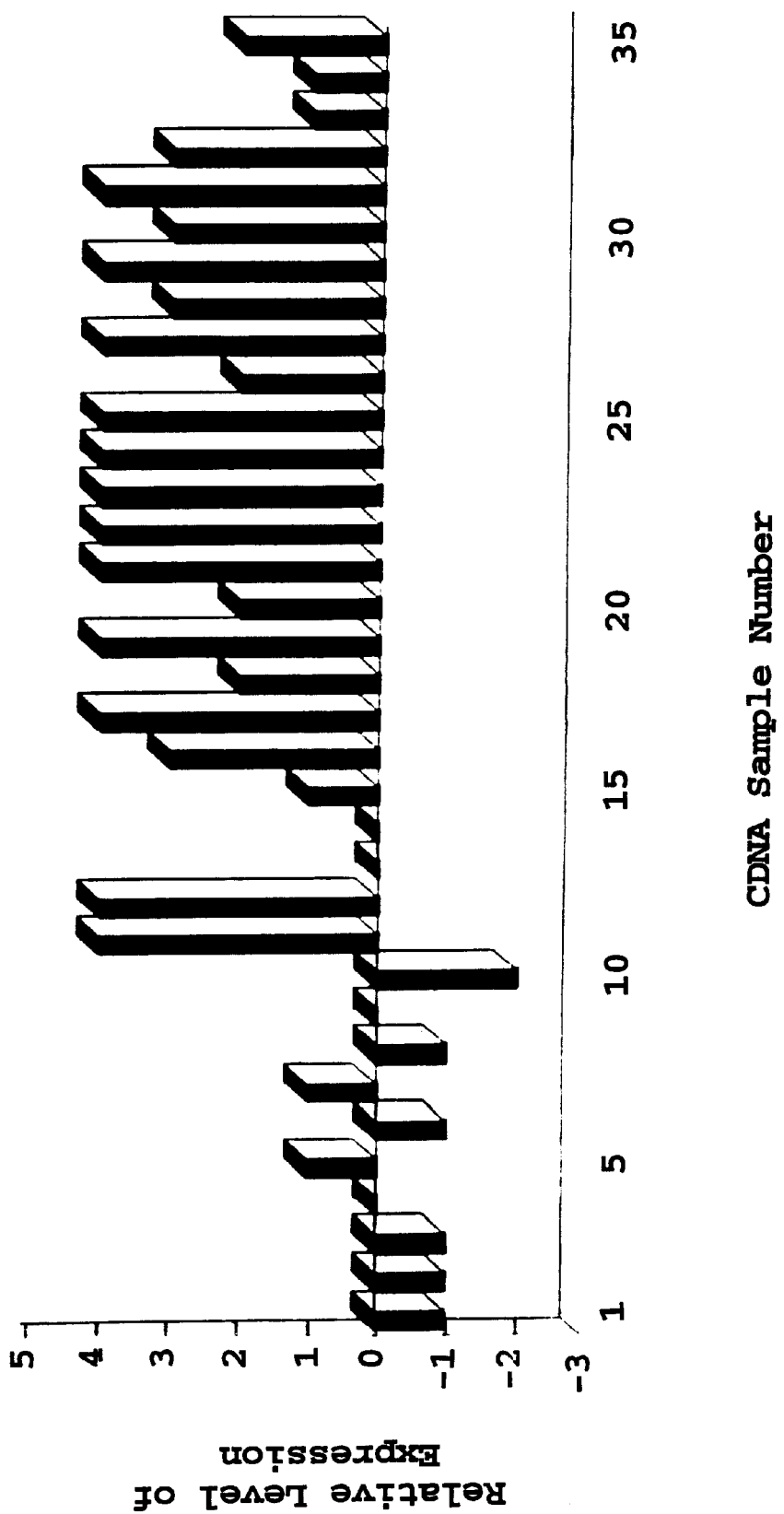
FIG. 4 is a graphical representation of the data from table 1 (quantitative PCR results for the TADG7 gene expression) showing that the TADG7 gene is over expressed in tumor cDNA and that high levels of over expression occur in the high malignant category ovarian tumors relative to normal ovary.
Figure 5:
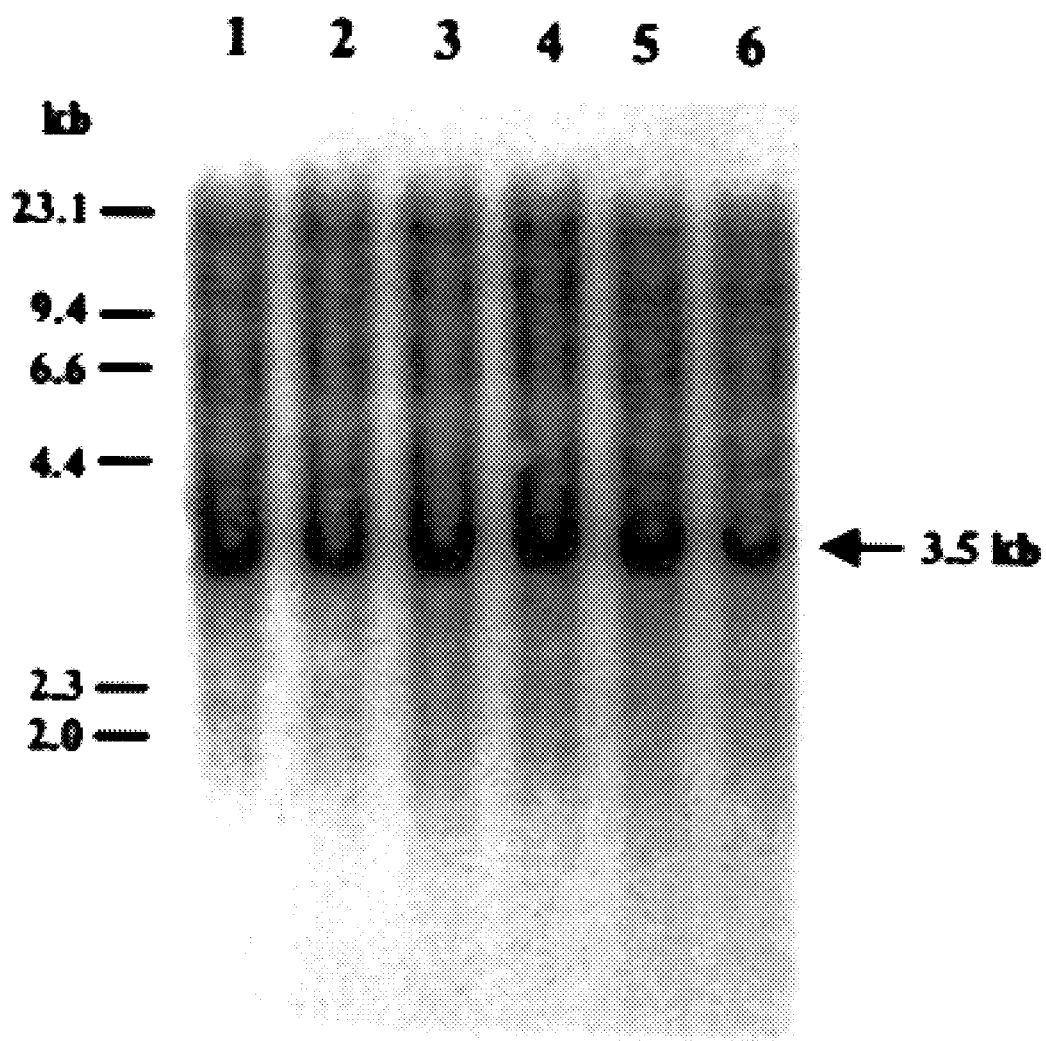
FIG. 5 is a Southern blot analysis using the 700 base pair probe of FIG. 2, which detected a single 3.5 kb band after restriction of DNA from multiple samples.
Figure 6A:
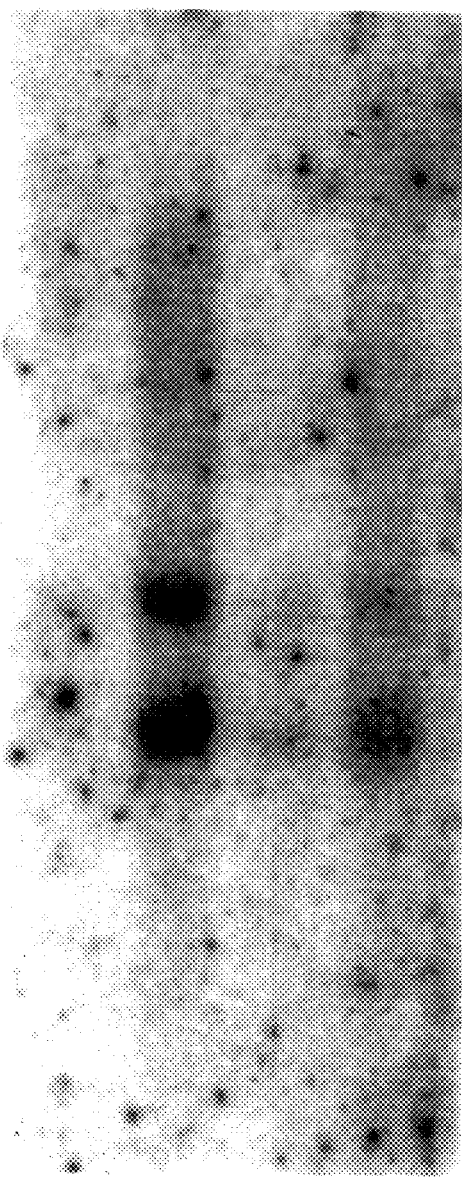
FIG. 6a shows a Northern blot analysis using the same probe to detect mRNA in adult spleen, thymus, pancreas, and testes showing thymus and testes to display dual bands 1.8 kb and 2.7 kb.
Figure 6B:
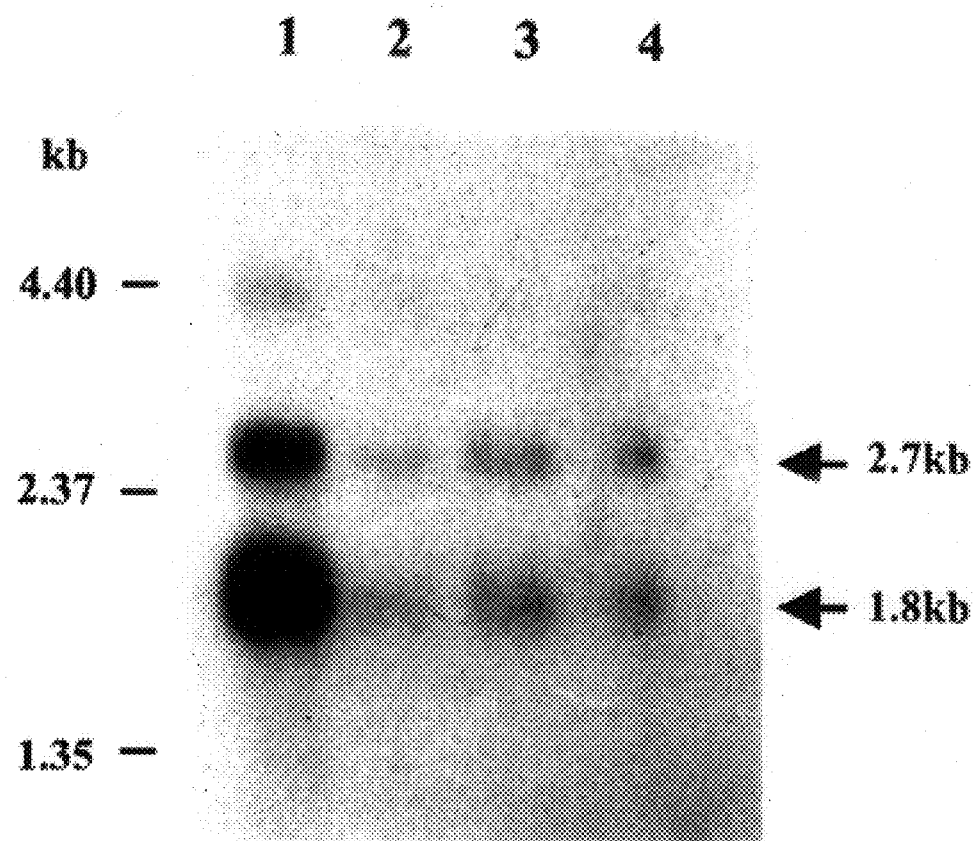
FIG. 6b is a blot of mRNA in fetal brain, lung, liver, and kidney.

The novel gene, named TADG7, was identified and isolated as a PCR product differentially displayed between normal and ovarian carcinoma mRNA, and amplified using the polymerase chain reaction (PCR) with primers as shown in FIG. 2 (Seq. I.D. Nos.4 and 5). The primers are redundant to a co-purifying protein or CA125. The results are shown in FIG. 1. The primer sequences are shown in FIG. 2. The PCR band was selected, based on differential expression in tumor cDNA, and subcloned as a 700 base pair amplified PCR product and sequenced. An approximately 550 bp PCR product from TADG7 mRNA, corresponding to the middle portion of the subcloned 700 bp band, was amplified by quantitative PCR to show that the novel TADG7 gene is differentially expressed in normal and tumor tissues as an approximately 3.5 kb mRNA (See FIGS. 3a and 3b comparing normal ovary to ovarian carcinomas). Table 1 shows data for expression of the TADG7 gene in 25 tumors (2 benign, 7 low malignant potential and 16 overt carcinomas). The results are graphically represented in FIG. 4. The TADG7 gene was shown to be present in multiple samples by Southern blot analysis of restricted DNA samples using the 700 bp probe as shown by the single 3.5 kb band. Results are shown in FIG. 5. Northern analysis using the same probe detected mRNA showing that the gene is over expressed in adult thymus (lane 2) and also present at low levels in pancreas and testes (lanes 3 and 4) tissues, as indicated by the dual 1.8 and 2.7 kb bands as shown in FIG. 6a. In FIG. 6b results are illustrated for fetal brain, lung, liver, and kidney. Over expression is observed in lane 1 for fetal brain.

TABLE 1

Quantitative PCR results for TADG7 expression levels in normal ovaries and ovarian tumor tissues

| cDNA | Tissue | Histology | Stage | Grade | TAGD7/Tublin | Stats |
|---|---|---|---|---|---|---|
| 1 | 768 | Normal | — | — | 0.07 | −1 |
| 2 | 430 | Normal | — | — | 0.06 | −1 |
| 3 | 773 | Normal | — | — | 0.11 | −1 |
| 4 | 782 | Normal | — | — | 0.13 | 0 |
| 5 | 868 | Normal | — | — | 0.24 | 1 |
| 6 | 673 | Normal | — | — | 0.11 | −1 |
| 7 | 456 | Normal | — | — | 0.19 | 1 |
| 8 | 858 | Normal | — | — | 0.11 | −1 |
| 9 | 660 | Normal | — | — | 0.16 | 0 |
| 10 | 856 | Normal | — | — | 0.01 | −2 |
| 11 | 1065 | Benign Serous | — | — | 0.93 | 4 |
| 12 | 646 | Benign Serous | — | — | 0.40 | 4 |
| 13 | 1031 | LMP Serous | 1 | 1 | 0.10 | 0 |
| 14 | 794 | LMP Serous | 1 | 1 | 0.11 | 0 |
| 15 | 1036 | LMP Mucinous | 1 | 1 | 0.22 | 1 |
| 16 | 481 | LMP Mucinous | 1 | 1 | 0.37 | 3 |
| 17 | 1101 | LMP Serous | 1 | 1 | 0.58 | 4 |
| 18 | 919 | LMP Mucinous | 1 | 1 | 0.26 | 2 |
| 19 | 1122 | LMP Serous | 3 | 1 | 0.50 | 4 |
| 20 | 643 | Cancer Serous | 3 | — | 0.30 | 2 |
| 21 | 515 | Cancer Serous | 3 | 1 | 0.95 | 4 |
| 22 | 1039 | Cancer Serous | 3 | 3 | 0.47 | 4 |
| 23 | 1035 | Cancer Sero/Endo | 2 | 1 | 0.59 | 4 |
| 24 | 1032 | Cancer Serous | 3 | 2 | 0.46 | 4 |
| 25 | 475 | Cancer Serous | 1 | 3 | 0.63 | 4 |
| 26 | 482 | Cancer Serous | 3 | 3 | 0.31 | 4 |
| 27 | 1118 | Cancer Serous | 3 | 3 | 1.24 | 4 |
| 28 | 464 | Cancer Serous | 3 | 3 | 0.36 | 3 |
| 29 | 465 | Cancer Serous | 3 | 3 | 1.21 | 4 |
| 30 | 1245 | Cancer Serous | 3 | 2 | 0.36 | 3 |
| 31 | 480 | Cancer Endo | 3 | 3 | 0.46 | 4 |
| 32 | 484 | Cancer Mucinous | 3 | 2 | 0.33 | 3 |
| 33 | 1246 | Cancer Mucinous | 3 | 1 | 0.22 | 1 |
| 34 | 1243 | Cancer Mucinous | 1 | 2 | 0.24 | 1 |
| 35 | 1244 | Cancer Mucinous | 3 | 2 | 0.26 | 2 |

Gene Sequencing

Figure 7:
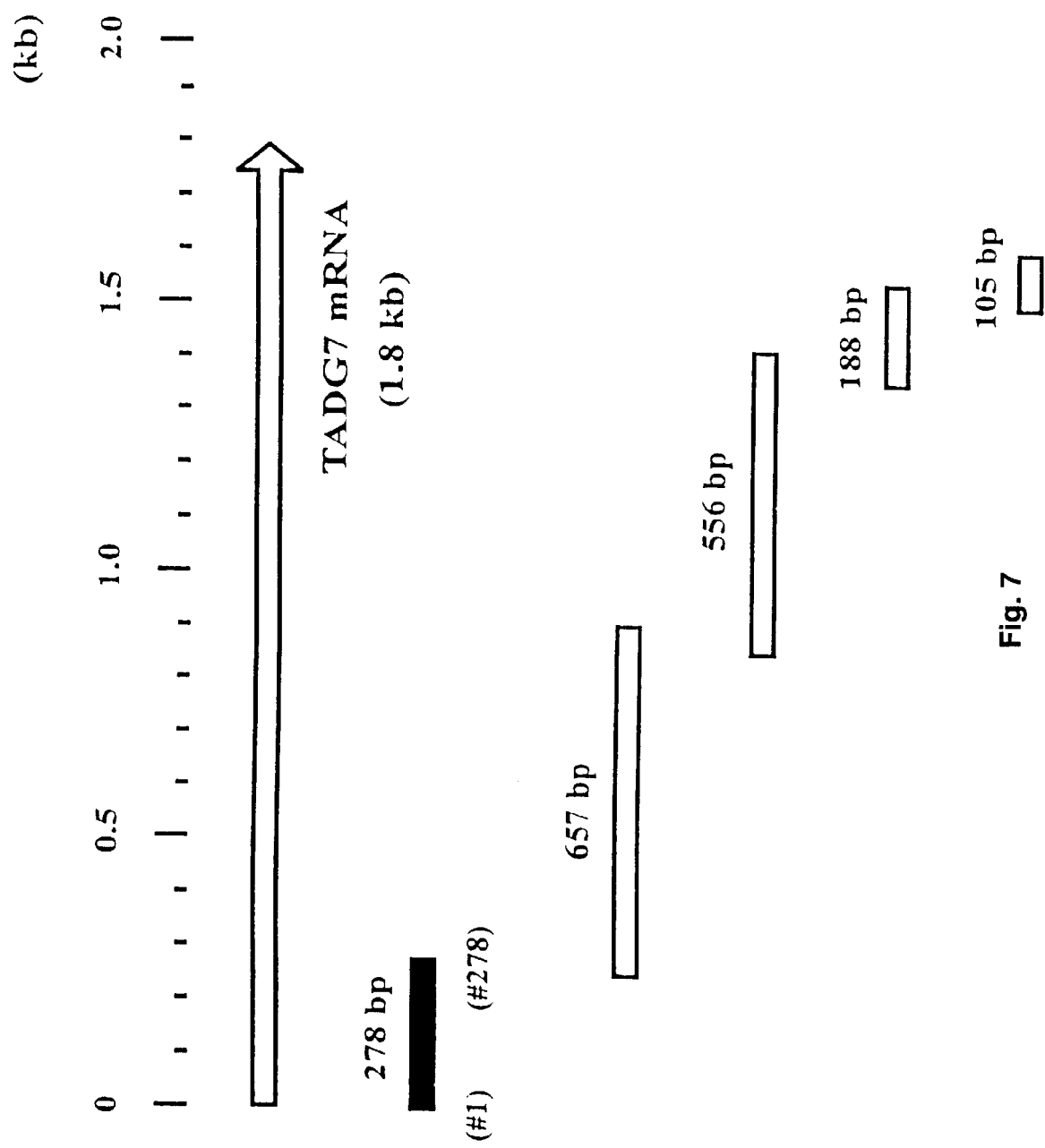
FIG. 7 is a diagram of the extension sequences with the overlapping illustrated.
Figure 8:
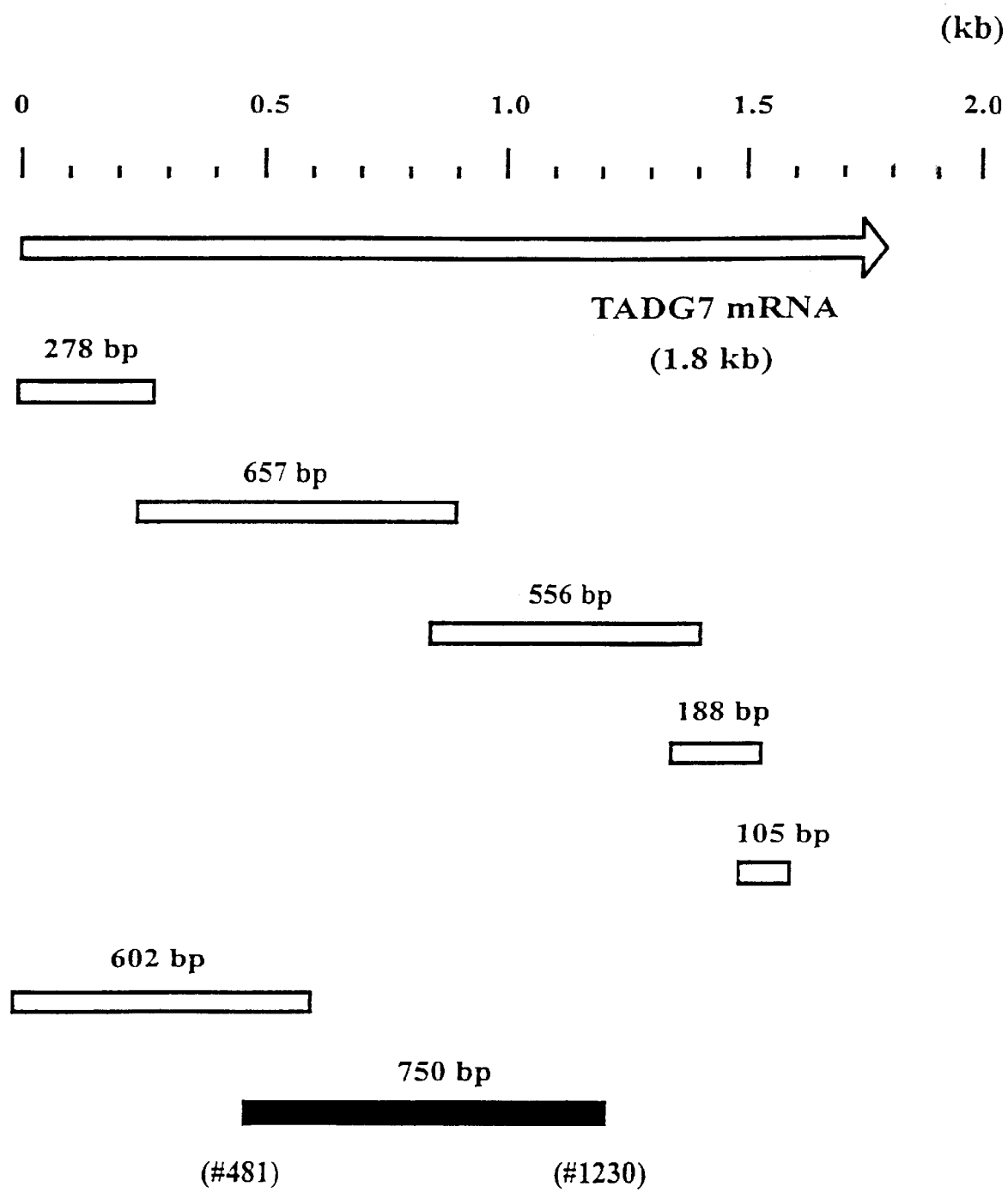
FIG. 8 is a diagram of two overlapping cloned sequences covering approximately 1230 base pairs.

TADG7 gene was identified and sequenced through a series of primer extension-type PCR experiments at the 3' end using oligo-dT and using an anchor sequence with a lung cDNA library at the 5' end. A diagram of the extension sequences with the overlapping sequences are shown in FIG. 7. An ovarian tumor tissue cDNA library was screened using the 700 base pair probe described above. Two overlapping sequences were cloned that cover approximately the first 1,230 bases the sequence. These overlapping sequences are diagramed in FIG. 8. Complete sequence of the 1609 base pair gene is shown in FIG. 9 and Seq. ID No. 2. A human partial cDNA clone of TADG-7 corresponding to nucleotides 26 to 1526 of SEQ ID No. 2 was inserted into the pGEM T-vector and deposited with the American Type Culture Collection (ATCC Patent Deposit Designation PTA-2926).

Figure 11:
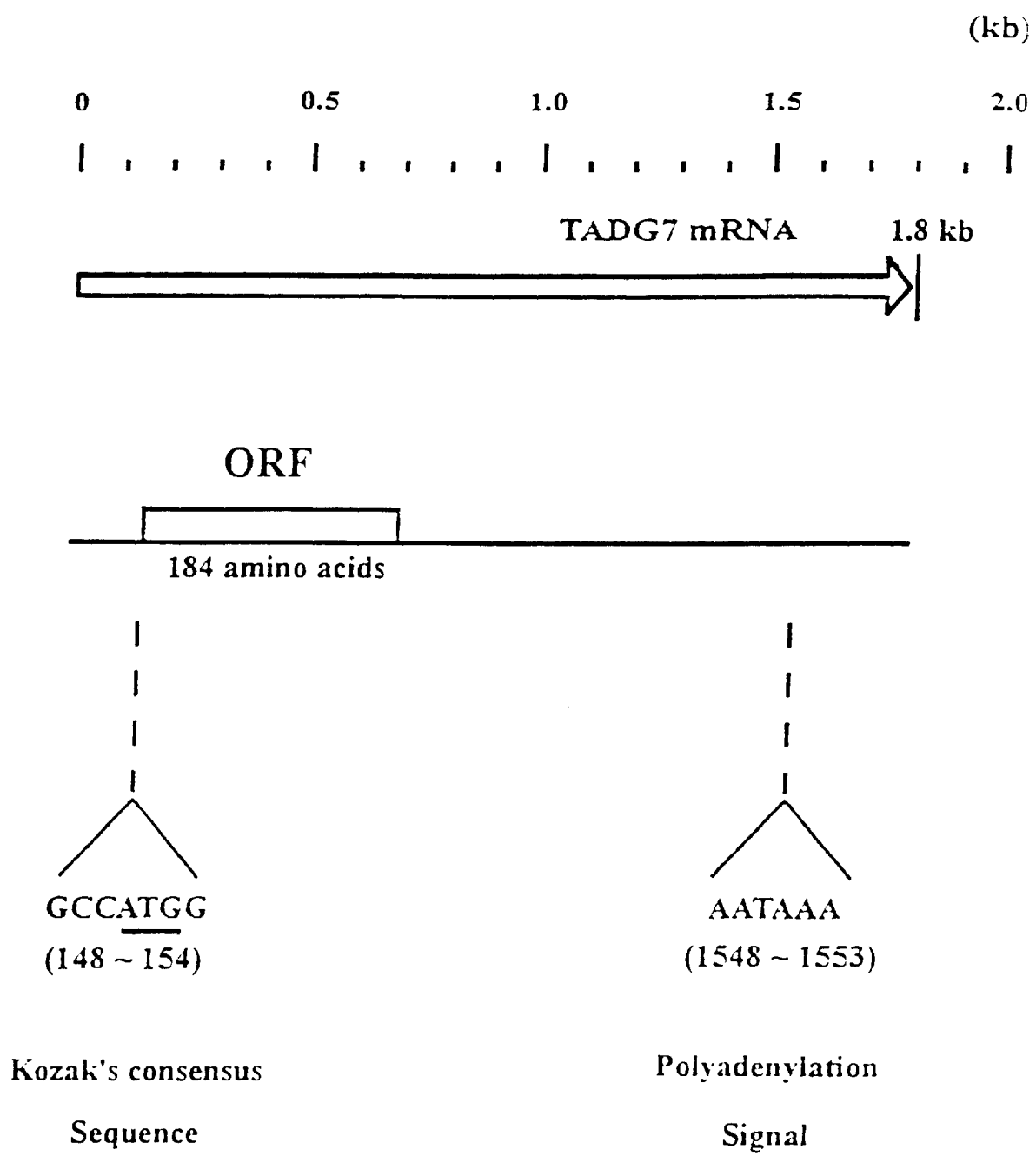
FIG. 11 Is a diagram of the gene indicating the position of the open reading frame, the Kozak's consensus sequence and the polyadenylation signal site.

The 3' end of the sequence is homologous at a homology rate of 97 and 96 percent to two sequences in the EST gene bank database, as noted above. One sequence is 405 base pair and the other is a 374 base pair sequence. Both of these sequences overlap the individual extension sequences that were developed and recognized originally by PCR. In FIGS. 10A and 10B the open reading frame is shown, coding for a 184 amino acid, 20.2 kDa protein extending from base 151 to base 705. Even though four methionine codons, ATG are at positions 141, 151, 164, and 178, the codon beginning at base 151 seems most appropriate for the start codon based on its context GCCATGG with the Kozak's consensus sequence. A diagrammatic presentation of the gene is shown in FIG. 11 indicating the position of the open reading frame, the Kozak's consensus sequence and the polyadenylation signal site.

The TADG7 Protein

The invention provides an isolated and purified TADG7 DNA sequence coding for the TADG7 protein. As noted above the open reading frame of the TADG7 nucleotide sequence predicts a 184 amino acid protein with the initial codon for methionine at position 151 of the sequence and continuing on through base 705. Examination of the 184 amino acid sequence does not disclose a definitive homology with any known functional domains. The highest overall homology to the TADG7 was exhibited by the receptor tyrosine kinase class III of the protein kinase family. Features of the translated protein include an RTK protein kinase signature (ATP binding site consensus) sequence, a potential RTK signature sequence for class III RTKs, three potential myristalation sites, four potential phosphorylation sites for protein kinase C and two potential phosphorylation sites for cyclic-AMP-dependent protein kinase as indicated in FIG. 12. In FIG. 12 numeral 1 marks the protein kinase C phosphorylation site, numeral 2 indicates the cyclic-AMP-dependent protein kinase phosphorylation site. Numeral 3 indicates a consensus myristylation site while numeral 4 indicates the RTK protein kinase signature (ATP binding site) and numeral 5 identify the class III RTK signature.

Production of TADG7 Protein and Expression Vectors

The invention provides a method of producing the TADG7 protein. For example, after synthesizing specific primers to allow amplification of the complete open reading frame sequence (See Table 1), the TADG7 DNA sequence can be integrated into a vector, and the TADG7 protein expressed in a chimeric cell using standard techniques as set out in "Molecular Cloning, A Laboratory Manual", 2nd Edition, Cold Spring Harbor Laboratory Press (1989) Optionally the protein may be expressed as a fusion product such as with the carboxyl terminal region of the glutathione S-transferase ("GST") protein using a chimeric cell, such as an *E. coli* bacterial expression system.

The cDNA coding for the TADG7 protein is preferably inserted into an expression vector and expressed in a suitable host cell. The promoter useful in the present invention may be any that allows regulation of the transcription of the TADG7 cDNA. Preferably, the promoter is selected from the group of Ptac or lac incorporated in the pGEX series of expression vectors available from Pharmacia of Uppsala Sweden. Pharmacia may also be contacted via the internet at http://www.biotech.pharmacia.se. Thus, many different promoters are known to those skilled in this art but the inventors prefer to use the above listed promoters for expression in *E. coli* with the pGEX vector series. The signal sequence useful in the present method may be any that contains a translation initiation codon and secretory signal together with part of a coding region for any highly expressed endogenous gene, preferably those of the pGEX vector series.

The linker sequence useful in the present method contains a recognition sequence for any proteolytic enzyme, preferably a thrombin recognition sequence, as in the pGEX vector series.

The transcription termination sequence useful in the present method may be any that allows stabilization and correct termination of the TADG7 mRNA transcripts. Preferably, the transcription termination sequence is one of those available for the pGEX vector series.

The selectable marker gene useful in the method of the present invention may be any that permits isolation of cells transformed with a TADG7 cDNA plasmid. Preferably, the selectable marker gene is selected from pyr4, pyrG, argB, trpC, amdS, or phleomycin or other antibiotic resistance genes.

Additionally, recombinant production of TADG7 protein is described below in its preferred embodiments. TADG7 can be produced in a number of host cells such as Aspergillus; *Saccharomyces cerevisiae, Kluyveromyces lactis,* or *Pichia pastorsis;* insect cells such as SF9; and mammalian cells such as Cos cells, Hela cells or the breast cancer tissue cell lines 231 and 435S as well as prokaryotic cells such as *E. coli*. The host cells, preferably *E. coli.* or mammalian cell lines, useful in the present invention are any that allow for integration of a vector, preferably a plasmid comprising the TADG7 cDNA and expression of the TADG7 cDNA, The isolated DNA of Seq. I.D. No. 1 was inserted into an expression vector comprising a promoter, an initiation sequence, a DNA segment coating for GST, a linker, an a selection marker gene. The vector was inserted into *E. coli* and expressed. Molecular weight determination performed by using polyacrylamide gel electrophoresis confirmed expression of an anticipated 30 kd protein for the GST gene alone and a predicted 40 kd fusion product for the GST-TADG7.

The invention further provides generation of antibodies against peptides of the novel protein. For example, peptides synthesized from the amino terminal end of the TADG7 amino acid sequence were used to raise polyclonal antibodies which in turn were used to confirm expression of TADG7 as a GST fusion protein in *E. coli*. Western analysis of the fusion protein confirmed the expression of this protein in this particular expression system. Other polyclonal antibodies developed against peptides to the various functional domains also allow the identification of interacting proteins and nucleotide sequences with the TADG7 protein.

The invention further provides a method of using the novel protein produced and isolated by the above method. The isolated protein is hydrolyzed, for example, with pepsin, trypsin, chymotrypsin, elastase, carboxypeptidase, aminopeptidase and dipeptidase to produce smaller peptide fragments and individual amino acids, in order to provide essential and nonessential amino acids of nutritional importance (Harper, A. E. Amino acids of nutritional importance.

In Toxicants occurring naturally in foods, ed. Committee on Food Protection, Food and Nutritional Board, National Research Council, 2nd ed. Washington, D.C.: National Research Council, 1973).

Definitions

The term "substitution analog" or "allelic variation" or "allelic variant" all refer to a DNA sequence which one or more codons specifying one or more amino acids of TADG7 or a TADG7 polypeptide are replaced by alternate codons that specify the same amino acid sequence with a different DNA sequence. Where "substitution analog" or "allelic variant" refers to a protein or polypeptide it means the substitution of a small number, generally five or less amino acids as are known to occur in allelic variation in human and other mammalian proteins wherein the biological activity of the protein is maintained.

The term "vector(s)" means plasmid, cosmid, phage or any other vehicle to allow insertion, propagation and expression of TADG7 cDNA.

The term "host(s)" means any cell that will allow TADG7 expression.

The term "promoter(s)" means regulatory DNA sequences that control transcription of the TADG7 cDNA.

The term "transformation" means incorporation permitting expression of heterologous DNA sequences by a cell.

The term "polypeptide" or "polypeptides" means several amino acids attached together to form a small peptide or polypeptide.

"Chimeric cell" means a cell whose DNA has been altered compared to a normal cell of the same organism.

"DNA coding for a protein" means DNA sequences which produce a particular primary amino acid sequence.

Preparation of Substitution Analogs

Due to the redundancy of the DNA code there are millions of DNA sequences that would produce a particular amino acid sequence when expressed. Given the amino acid sequence, for example Seq. I.D. No. 1, one can substitute into the natural DNA sequence, such as Seq. I.D. No. 2, alternative codons for the desired amino acids to produce an alternative DNA sequence also coding for the novel protein. One may find that particular chimeric cells of a particular expression method favor particular mRNA codons for a particular amino acid. Altering the human DNA sequence to increase the frequency of favored codons may improve the expression efficacy in a chimeric cell, thus improving the efficacy of the expression process. The sequences may be derived by substitution of redundant codons for the amino acid sequences and splicing the substituted sequences into the natural gene by routine methods well known in the art. It is impractical to attempt to list all the millions of DNA sequences that may code for the claimed sequence. However, the invention comprises the novel protein, its novel amino acid sequence, and all DNA sequences natural or synthetic coding for the novel amino acid sequence. These substitution analogs may be constructed in the following manner: Table 2 lists the alternative codons that code for the 20 common amino acids. DNA sequence substitution analogs that also code for human TADG7 can be constructed by choosing alternate codons from Table 2 to alter the DNA Sequence between a pair of restriction enzyme cleavage sites, as are well known in the art. Alternative codons are assembled into a synthetic oligonucleotide by conventional methods and the synthetic oligo is substituted into the endonuclease treated DNA of Sequence ID. No. 2 by the methods described in "Molecular Cloning, A Laboratory Manual", 2d Edition, Cold Spring Harbor Laboratory Press (1989), to produce a substitution analog. Other methods generally known to those skilled in the art can also be employed to obtain substitution analogs of DNA sequences. The alteration of the DNA by cleavage and codon substitution maybe repeated to substitute substantial portions of the original DNA sequence with alternative codons without altering the protein amino acid sequence of Sequence ID. No. 1. Alteration of a DNA sequence which produces no change in the protein expressed by the DNA sequence might, for example, be conducted to increase protein expression in a particular host cell by increasing the occurrence of codons that correspond to amino acid tRNAs found in higher concentration in the host cell. Such altered DNA sequences for substitution analogs can be easily produced by those of ordinary skill in the art following the method set out above, or other alternative techniques for altering the DNA sequence while obtaining the same protein on expression. Substitution analogs can be obtained by substitution of oligonucleotides at restriction cleavage sites as described above, or by other equivalent methods that change the codons while preserving the amino acid sequence of the expressed protein.

| Amino Acid | One Letter Symbol | 3 Letter Symbol | DNA CODON |
|---|---|---|---|
| Alanine | A | ala | GCT, GCC, GCA, GCG |
| Arginine | R | arg | CGT, CGC, CGA, CGG, AGA, AGG |
| Asparagine | N | asn | AAT, AAC |
| Aspartic Acid | D | asp | GAT, GAC |
| Cysteine | C | cys | TGT, TGC |
| Glutamic Acid | E | glu | GAA, GAG |
| Glutamine | Q | gln | CAA, CAG |
| Glycine | G | gly | GGT, GGC, GGA, GGG |
| Histidine | H | his | CAT, CAC |
| Isoleucine | I | ile | ATT, ATC, ATA |
| Leucine | L | lue | TTA, TTG, CTT CTC, CTA, CTG |
| Lysine | K | lys | AAA, AAG |
| Methionine | M | met | ATG |
| Phenylalanine | F | phe | TTT, TTC |
| Proline | P | pro | CCT, CCC, CCA, CCG |
| Serine | S | ser | TCT, TCC, TCA, TCG, AGT, AGC |
| Threonine | T | thr | ACT, ACC, ACA, ACG |
| Tryptophan | W | trp | TTG |
| Tyrosine | Y | tyr | TAT, TAC |
| Valine | V | val | GTT, GTC, GTG, GTG |

Antibody Production

An antigenic peptide (SEQ ID NO:5 containing residues 129 to 140 (TPF PGP LSG SNT) was synthesized commercially (Biosynthesis, Inc. Lewisville, Tex.) directly on a polylysine core matrix with 8 peptide arms to generate a high titer antibody. The resulting immunogen (TADG7 MAP) is composed of eight copies of a single epitope from the TADG7 protein attached to a non-immunogenic core matrix. To prepare an antigen/adjuvant mixture, TADG7 MAP antigen was dissolved in saline at a concentration of 0.10–0.50 mg per ml of saline, and the antigen solution was mixed with an equal volume of adjuvant solution (RIBI adjuvant system R-730, MPL+TDM+CWS Emulsion)(RIBI ImmunoChem Inc., Hamilton, Mont., USA) containing 0.5 mg each of monophospholipid A (MPL), trhalose dicorynomycolate (TDM) and cell wall skeleton (CWS) per ml of saline which also contains 4% squalene oil. The prepared TADG7-MAP antigen/adjuvant mixture was injected into a rabbit (total dose: 1 ml, intradermal: 0.3 ml divided into six sites, 0.4 ml divided into two hind legs, subcutaneous: 0.1 ml in the neck, and intraperitoneal injection: 0.2 ml) on day 0, and a boost injection was given on day 28. A test bleed was obtained on day 38 to 42. The serum drawn from the rabbit was used for immunohistochemistry as follows.

Figure 13A:
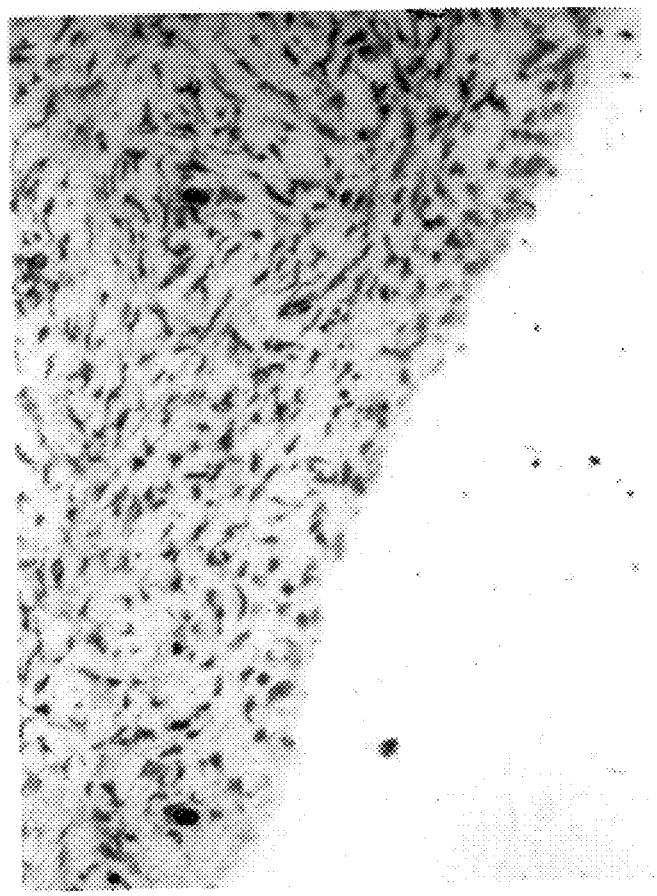
FIG. 13A shows that immunohistochemistry staining of normal ovarian epithelium with an antibody to TADG7 is negative in the stroma or epithelium.
Figure 13B:
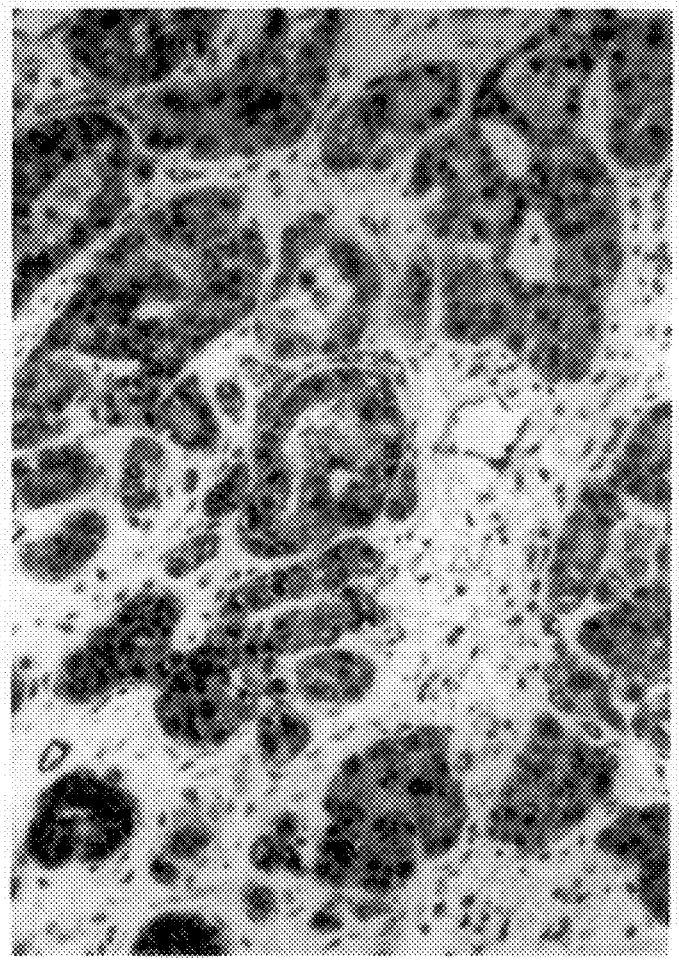
FIG. 13B shows strong immunohistochemistry staining in ovarian clear cell carcinoma.
Figure 13C:
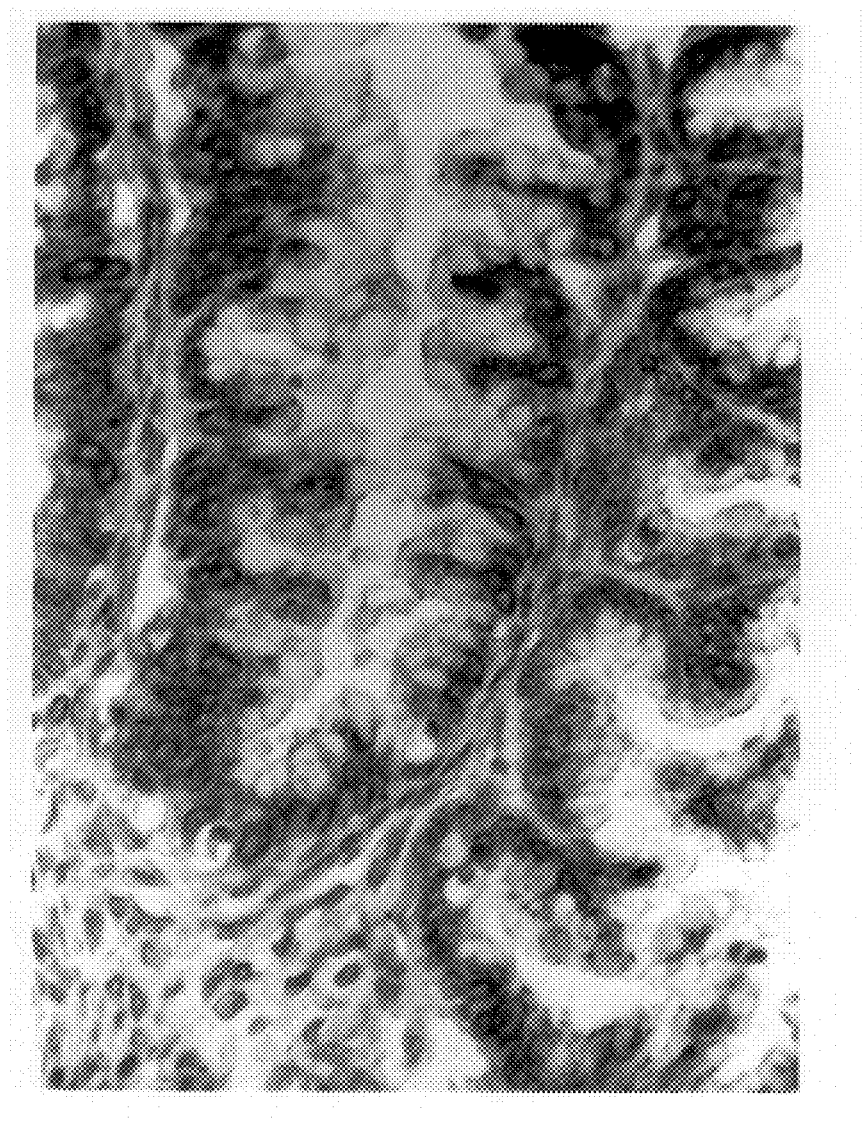
FIG. 13C shows strong immunohistochemistry staining in mucinous an carcinoma.

Immunohistochemistry staining was performed using a Vectstain Elite ABC kit (Vector). Formalin fixed and paraffin embedded specimens were routinely deparaffinized and processed using microwave heat treatment in 0.01 M sodium citrate buffer (pH 6.0). The specimen were incubated in methanol with 0.3% hydrogen peroxide ($H_2O_2$) for 30 minutes at room temperature and then incubated with normal horse serum for 30 minutes. The samples were incubated with anti TADG7 rabbit polyclonal antibody (diluted 1:100) for 1 hour at room temperature in a moisture chamber, followed by an incubation with a second biotinylated anti-rabbit IgG for 30 minutes, then incubated with ABC reagent (Vector) for 30 minutes, The final products were visualized by using the ABC substrate system (Dako) and sections counterstained with hemotoxylin before mounting. Negative controls were performed by using normal serum in place of the primary antibody. As shown in FIG. 13 the TADG7 protein is strongly positive in tumor cells, whereas stromal cells are negatively stained. Normal ovarian epithelium does not stain for the TADG7 antigen. These data confirm that the TADG7 protein is deferentially expressed in normal and tumor cells and thus is a marker protein for ovarian tumors. The invention provides a method for detecting ovarian tumor by detecting the expression of the TADG7 protein.

The foregoing illustrate the invention an is not intended to limit the invention. Those skilled in the art will recognize that many variations are possible in using the invention described above, which is defined and limited by the claims set out below.

We claim:

1. A purified and isolated DNA molecule coding for a protein, wherein said protein consists of the amino acid sequence shown in SEO ID NO: 1.

2. The purified and isolated DNA molecule of claim 1, wherein said DNA consists of the sequence shown in SEQ ID NO: 2.

3. A vector comprising the purified and isolated DNA molecule of claim 1 operably linked to a promoter.

4. A host cell comprising the purified and isolated DNA molecule of claim 1.

5. A host cell comprising the purified and isolated DNA molecule of claim 2.

6. A host cell comprising the vector of claim 3.

7. A method of producing a protein, wherein said protein consists of the amino acid sequence shown in SEQ ID NO: 1, comprising the step of:

expressing a DNA molecule in a host cell, wherein said DNA molecule encodes said protein, and wherein the expression of said DNA molecule leads to the production of said protein.

8. The method of claim 7, wherein said DNA molecule consists of the sequence shown in SEQ ID NO: 2.

* * * * *